(12) United States Patent
Lim et al.

(10) Patent No.: US 10,990,007 B2
(45) Date of Patent: Apr. 27, 2021

(54) MULTI FUNCTION PHOTOACID GENERATOR AND CHEMICALLY AMPLIFIED PHOTORESIST COMPOSITION FOR THICK LAYER COMPRISING THE SAME

(71) Applicant: LG CHEM, LTD., Seoul (KR)

(72) Inventors: Min Young Lim, Daejeon (KR); Tae Seob Lee, Daejeon (KR); Hyun Min Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/489,560

(22) PCT Filed: Aug. 24, 2018

(86) PCT No.: PCT/KR2018/009822
§ 371 (c)(1),
(2) Date: Aug. 28, 2019

(87) PCT Pub. No.: WO2019/045377
PCT Pub. Date: Mar. 7, 2019

(65) Prior Publication Data
US 2020/0033725 A1    Jan. 30, 2020

(30) Foreign Application Priority Data

Sep. 4, 2017 (KR) .................. 10-2017-0112690

(51) Int. Cl.
*G03F 7/004* (2006.01)
*C07D 221/14* (2006.01)
*G03F 7/039* (2006.01)

(52) U.S. Cl.
CPC ......... *G03F 7/0045* (2013.01); *C07D 221/14* (2013.01); *G03F 7/0392* (2013.01)

(58) Field of Classification Search
CPC .................................................. C07D 221/14
See application file for complete search history.

(56) References Cited

U.S. PATENT DOCUMENTS

| | | |
|---|---|---|
| 2010/0028807 A1 | 2/2010 | Takemoto et al. |
| 2012/0289697 A1 | 11/2012 | Murai et al. |
| 2015/0299132 A1 | 10/2015 | Hirahara et al. |
| 2016/0085148 A1 | 3/2016 | Zhang et al. |
| 2017/0003587 A1 | 1/2017 | Zhang et al. |

FOREIGN PATENT DOCUMENTS

| | | |
|---|---|---|
| JP | 2013-001821 A | 1/2013 |
| JP | 2017-197641 A | 11/2017 |
| KR | 10-2012-0114353 A | 10/2012 |
| KR | 10-2015-0087846 A | 7/2015 |
| KR | 10-2016-0048144 A | 5/2016 |
| KR | 10-2017-0042726 A | 4/2017 |
| WO | 2016-043558 A | 3/2016 |
| WO | 2016-043941 A1 | 3/2016 |

OTHER PUBLICATIONS

International Search Report and Written Opinion issued for International Application No. PCT/KR2018/009822 dated Dec. 6, 2018, 11 pages.

*Primary Examiner* — Noble E Jarrell
(74) *Attorney, Agent, or Firm* — Rothwell, Figg, Ernst & Manbeck, P.C.

(57) ABSTRACT

The present invention relates to a photoacid generator, and a chemically amplified photoresist composition for a thick film including the same, wherein the photoacid generator has excellent solubility and sensitivity, and also has an anti-corrosion effect, in addition to the effect as a photoacid generator. Thus, a chemically amplified photoresist composition for a thick film including the photoacid generator reduces scum and/or footing at the exposed part after development. The photoacid generator represented by the following Chemical Formula 1:

[Chemical Formula 1]

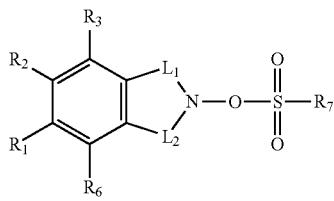

In Chemical Formula 1, the definition of each substituents is the same as the detail description of the specification.

10 Claims, No Drawings

MULTI FUNCTION PHOTOACID GENERATOR AND CHEMICALLY AMPLIFIED PHOTORESIST COMPOSITION FOR THICK LAYER COMPRISING THE SAME

CROSS-REFERENCE TO RELATED APPLICATION(S)

This application is a 35 U.S.C. § 371 National Phase Entry Application from PCT/KR2018/009822, filed on Aug. 24, 2018, and designating the United States, which claims the benefit of Korean Patent Application No. 10-2017-0112690 filed on Sep. 4, 2017 with the Korean Intellectual Property Office, the disclosures of which are herein incorporated by reference in their entirety.

TECHNICAL FIELD

The present invention relates to a photoacid generator, and a chemically amplified photoresist composition for a thick film including the same.

BACKGROUND ART

With expansion of application of miniaturization technology for a FAB process, packaging technology has also been changed to a process technology for the preparation of high performance, thin, short, and small packages. Particularly, with the increase in semiconductor input/output terminals, the use of flip chips has expanded and FOWLP technology has been introduced, and a TSV process capable of direct connection between chips has expanded for the minimization of signal delay, and thus there is increasing demand for bumping, and the development of bump PR technology is very important.

Bump PR should have excellent sensitivity and resolution in a thick film of 10 μm to 100 μm, and it should have good patterning performance such as good properties of straightness, residue, footing, notching, etc., and excellent resistance to a plating solution so as to form a metal bump through a plating process.

Thus, in order to increase sensitivity and resolution in a thick film, a chemically amplified photoresist is used, and the composition is known to include a resin that is dissociated by an acid to increase solubility to an alkali developing solution, a photosensitive acid generator (photoacid generator), an acid diffusion inhibitor, an anti-corrosive agent, and specific dissolution inhibitors.

According to the prior art, a naphthalimide-type photoacid generator is used, and in this case, since the solubility is not good, the content is increased so as to increase sensitivity, but this has a limitation that a scum remains at the exposed part after development. Thus, there is a demand for studies on photoacid generators that are capable of improving the disadvantages.

DETAILED DESCRIPTION OF THE INVENTION

Technical Problem

It is an object of the present invention to provide a photoacid generator that has excellent solubility and sensitivity, and also exhibits an excellent anti-corrosion effect, in addition to the effect as a photoacid generator.

It is another object of the present invention to provide a chemically amplified photoresist composition for a thick film including the photoacid generator.

Technical Solution

According to one embodiment of the present invention, a photoacid generator represented by the following Chemical Formula 1 is provided.

[Chemical Formula 1]

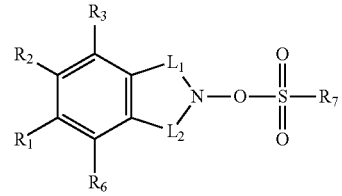

In Chemical Formula 1, $R_1$, $R_2$, and $R_6$ are each independently, hydrogen, a halogen, a thiol(SH), a $C_{1-10}$ alkyl group, a $C_{1-10}$ fluoroalkyl group, a $C_{1-10}$ alkoxy group, a $C_{1-10}$ alkylthio group, or a $C_{1-10}$ alkyl group substituted with one or more $C_{1-20}$ alkylene dithiol groups, at least one of $R_1$, $R_2$, and $R_6$ is a $C_{1-10}$ alkyl group substituted with one or more $C_{1-20}$ alkylene dithiol groups, $L_1$ is a substituted or unsubstituted $C_{1-4}$ alkylene group that includes or does not include a carbonyl connected to the nitrogen atom, or a carbonyl, $L_2$ is a carbonyl or methylene, $R_3$ is hydrogen, a $C_{1-20}$ aliphatic functional group, or it forms a $C_{6-20}$ aromatic ring or a $C_{5-20}$ aliphatic ring together with $L_1$, and $R_7$ is a $C_{1-10}$ alkylfluoro group, a $C_{1-10}$ alkoxy group, or a $C_{1-10}$ alkylthio group.

According to another embodiment of the present invention, a photoresist composition for a thick film including the photoacid generator is provided.

Hereinafter, a photoacid generator, a chemically amplified photoresist composition for a thick film including the photoacid generator, and a photoresist pattern prepared therefrom according to specific embodiments of the invention will be explained in detail.

Meanwhile, as used herein, the term "C1-20 alkylene dithiol group" means a functional group wherein a linear C1-20 alkylene group is positioned between two thiol groups, and a point where it bonds to another functional group is any one sulfur of the two thiol groups.

Further, as used herein,

means a bond connected to another substituent.

Photoacid Generator

The present inventors confirmed that in a chemically amplified photoresist composition for a thick film, if a conventional naphthalimide-type photoacid generator includes a $C_{1-10}$ alkyl group substituted with one or more alkylene dithiol groups, the solubility may be excellent, thus sensitivity may be increased, scum may not be generated at the exposed part after development, and an excellent anti-corrosion effect may be exhibited without a separate anti-corrosive agent, and completed the present invention.

Specifically, the photoacid generator of the present invention may be represented by the following Chemical Formula 1:

[Chemical Formula 1]

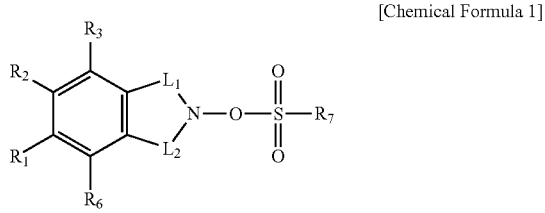

wherein, in Chemical Formula 1, $R_1$, $R_2$, and $R_6$ are each independently hydrogen, a halogen, a thiol (SH), a C1-10 alkyl group, a C1-10 fluoroalkyl group, a C1-10 alkoxy group, a C1-10 alkylthio group, or a C1-10 alkyl group substituted with one or more C1-20 alkylene dithiol groups, at least one of $R_1$, $R_2$, and $R_6$ is a C1-10 alkyl group substituted with one or more C1-20 alkylene dithiol groups, $L_1$ is a C1-4 substituted or unsubstituted alkylene group that includes or does not include a carbonyl, or a carbonyl connected to the nitrogen atom, $L_2$ is a carbonyl or methylene, $R_3$ is hydrogen, a C1-20 aliphatic functional group, or forms a C6-20 aromatic ring or a C5-20 aliphatic ring together with $L_1$, and $R_7$ is a C1-10 alkyl fluoro group, a C1-10 alkoxy group, or a C1-10 alkylthio group.

The photoacid generator according to one embodiment of the present invention has a structure represented by Chemical Formula 1, wherein at least one of $R_1$, $R_2$, and $R_6$ is a $C_{1-10}$ alkyl group substituted with one or more $C_{1-20}$ alkylene dithiol groups.

Meanwhile, according to one embodiment of the present invention, the C1-10 alkyl group may be linear-shaped, and may have a structure wherein two or more identical or different alkylene dithiol groups are substituted at identical or different positions of the linear chain.

Since the photoacid generator according to one embodiment of the present invention, due to the above described novel structure, has excellent solubility, and thus can increase sensitivity, and can exhibit excellent anti-corrosion effect, in addition to the effect as a photoacid generator, it has high applicability compared to the conventional naphthalimide-type photoacid generator. Particularly, the anti-corrosive replacement effect of the photoacid generator may be exhibited by the alkylene dithiol groups substituted at the linear alkyl group.

Further, the photoacid generator according to one embodiment of the present invention has a structure represented by Chemical Formula 1, wherein $R_3$ may be hydrogen or a C1-20 aliphatic functional group, or may form a C6-20 aromatic ring or a C5-20 aliphatic ring together with $L_1$. For example, the photoacid generator may have a structure represented by Chemical Formula 1, wherein $R_3$ and $L_1$ may form a 5-membered ring or 6-membered ring together.

Specifically, the photoacid generator according to one embodiment of the present invention may have a structure represented by Chemical Formula 1, wherein $R_3$ is connected with $L_1$ to form a C6-20 aromatic ring, and $R_3$ is a C6-20 alkenylene group including at least one double bond. For example, the formed aromatic ring may be benzene or naphthalene.

The photoacid generator according to another embodiment of the present invention may have a structure represented by Chemical Formula 1, wherein $R_3$ is connected with $L_1$ to form a C5-20 aliphatic ring, and $R_3$ is a C5-20 alkylene group. For example, the formed aliphatic ring may be cyclohexane.

Meanwhile, the photoacid generator according to one embodiment of the present invention has a structure of Chemical Formula 1, wherein $L_1$ is defined by the following Chemical Formula 2:

[Chemical Formula 2]

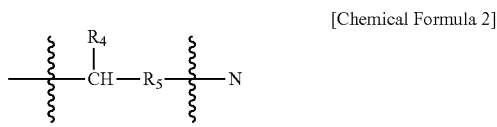

wherein, in Chemical Formula 2, $R_5$ is a $C_{1-3}$ alkylene group that includes or does not include a carbonyl connected to the nitrogen atom, or a carbonyl, and $R_4$ is hydrogen, a $C_{1-20}$ aliphatic functional group, or forms one or more rings selected from the group consisting of benzene, naphthalene, and cyclohexane together with $R_3$.

Specific examples of the photoacid generators as explained above may include compounds represented by the following Chemical Formulae 3 to 8, but the present invention is not limited thereby.

[Chemical Formula 3]

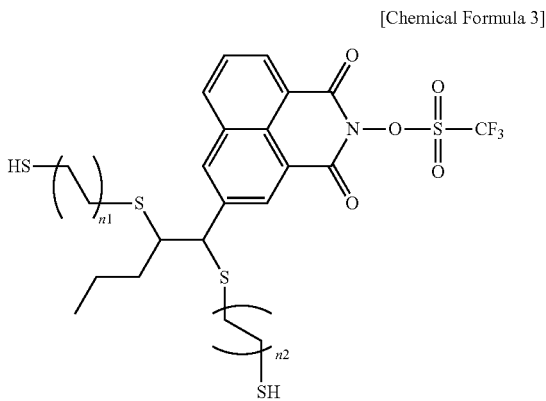

[Chemical Formula 4]

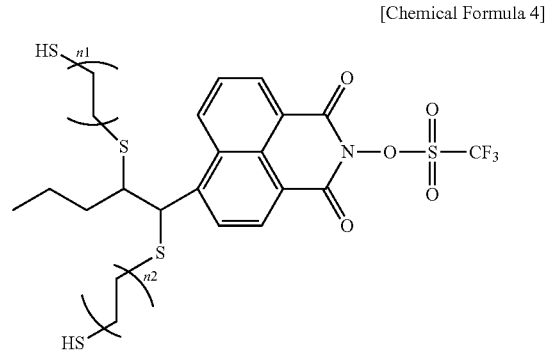

[Chemical Formula 5]

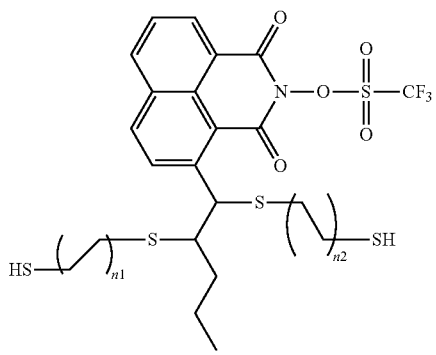

[Chemical Formula 6]

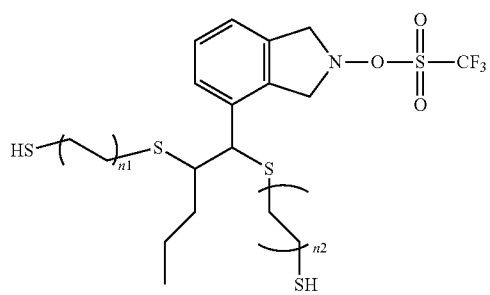

[Chemical Formula 7]

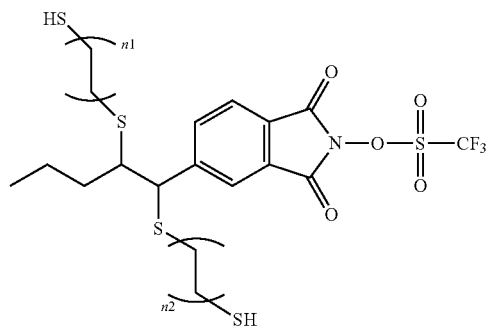

[Chemical Formula 8]

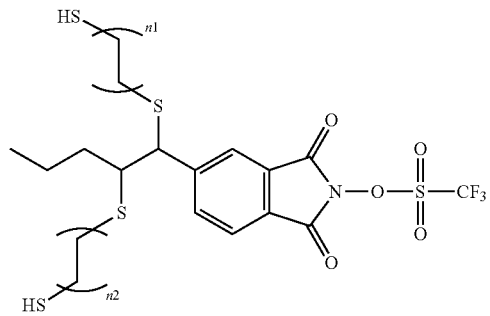

In Chemical Formulas 3 to 8, n1 and n2 are each independently an integer, and $1 \leq n1 \leq 20$ and $1 \leq n2 \leq 20$.

The synthesis of Chemical Formula 1 may be conducted by introducing a substituted or unsubstituted alkyl group having one or more double bonds or triple bonds in the conventional photoacid generator such as PG-1((trifluoromethylsulfonyloxy)-1,8-naphthalimide), and introducing one or more alkylene dithiol groups in the double bonds or triple bonds.

A Chemically Amplified Photoresist Composition for a Thick Film

The chemically amplified photoresist composition for a thick film according to another embodiment of the present invention includes the above-described photoacid generator.

In general, a chemically amplified photoresist composition for a thick film may include a resin that can be dissociated by an acid to increase solubility to an alkali developing solution, and a photoinitiator, in addition to a photoacid generator.

The resin that can be dissociated by an acid to increase solubility to an alkali developing solution is not specifically limited, as long as it is a polymer resin having an acid group protected by a protection group, and the acid group may be, for example, a carboxy group, a phenolic hydroxy group, etc. Meanwhile, as the resin, a polymer resin commonly known in the art may be used, and for example, it may be a novolac resin, a hydroxystyrene resin, an acrylic resin, etc., but it is not limited thereto.

As the photoinitiator, those commonly used in the art may be used, and it is not specifically limited. For example, the photoinitiator may be selected from benzophenone, aromatic α-hydroxyketone, benzyl ketal, aromatic α-aminoketone, a phenyl glyoxalic acid ester, a mono-acylphosphine oxide, a bis-acyl phosphine oxide, a tris-acyl phosphine oxide, an oxime ester derived from an aromatic ketone, and/or a carbazole-type oxime ester.

Further, the chemically amplified photoresist composition for a thick film may further include an acid diffusion inhibitor, a surfactant, an anti-corrosive agent, a dissolution inhibitor, a solvent, etc., in addition to the above components.

The acid diffusion inhibitor may be included for improvement in stability after exposure, resist pattern shape, etc., and for example, it may be one or more selected from the group consisting of triethylamine, tripropyl amine, tribenzyl amine, trihydroxyethyl amine, and ethylene diamine.

The anti-corrosive agent performs a function of minimizing the degree of corrosion of the metal pattern by a photoresist stripping composition, and those commonly used in the art may be used without specific limitations.

Meanwhile, the anti-corrosive agent may be, for example, a triazole-based compound, gallic acid (GA), or a mixture thereof. The anti-corrosive agent may be physically and chemically adsorbed to the metal constituting the metal pattern, thus preventing the corrosion of the metal pattern. For example, the triazole-based compound may include benzotriazole (BTA), tolytriazole (TTA), etc. However, if the photoacid generator according to the present invention is used, it may replace an anti-corrosive agent by the structure of Chemical Formula 1, and thus the anti-corrosive agent may not necessarily be used.

Meanwhile, as the dissolution inhibitor, those commonly known in the in the art may be used, without specific limitations.

The solvent may be included to uniformly dissolve and mix various components and control the viscosity of the photoresist composition, and it may be, for example, ketones such as acetone, methylethylketone, cyclohexanone, methyl isoamyl ketone, 2-heptanone, etc.; polyhydric alcohols and derivatives thereof such as ethylene glycol, ethylene glycol monoacetate, diethylene glycol, diethylene glycol monoacetate, propylene glycol, propylene glycol monoacetate, dipropylene glycol, monomethylether, monoethylether, monopropylether, monobutylether, monophenylether of dipropylene glycol monoacetate, etc.; cyclic ethers such as dioxane, etc.; esters such as ethyl formate, methyl lactate, ethyl lactate, methyl acetate, ethyl acetate, butyl acetate, methyl pyruvate, methyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoic acid, 3-methoxybutyl acetate, 3-methyl-3-methoxybutyl acetate, etc.; or aromatic hydrocarbons such as toluene, xylene, etc. They may be used alone or in combinations of two or more kinds thereof.

Meanwhile, in the chemically amplified photoresist composition for a thick film, based on 100 parts by weight of the resin dissociated by an acid to increase solubility to an alkali developing solution, the photoacid generator may be included in the content of 0.5 parts by weight to 10 parts by weight, the solvent may be included in the content of 1 parts by weight to 10 parts by weight, and the surfactant may be included in the content of 0.01 parts by weight to 1 part by weight. In addition, the acid diffusion inhibitor may be included in the content of 0.001 parts by weight to 0.1 parts by weight, based on 100 parts by weight of the photoacid generator. If the components are included in the photoresist composition in the above ranges, the solubility and sensitivity of the photoresist composition may be increased by the alkylene dithiol group, and an anti-corrosive replacement effect may be simultaneously exhibited, thus reducing scum and/or footing after development.

Advantageous Effects

The photoacid generator according to the present invention has excellent solubility and sensitivity, and also has excellent anti-corrosion effect, in addition to the effect as the photoacid generator.

Thus, a chemically amplified photoresist composition for a thick film including the photoacid generator may have reduced scum and/or footing at the exposed part after development.

DETAILED DESCRIPTION OF THE EMBODIMENTS

Although various modifications can be made to the present invention and the present invention may have various forms, specific examples will be illustrated and explained in detail below. However, it should be understood that these are not intended to limit the present invention to specific disclosures, and that the present invention includes all modifications, equivalents, or replacements thereof without departing from the spirit and technical scope of the invention.

Hereinafter, the action and effects of the present invention will be explained in more detail through specific examples. However, these examples are presented only as illustrations of the invention, and the scope of the right of the invention is not determined thereby.

Preparation Example of a Photoacid Generator

Preparation Example 1

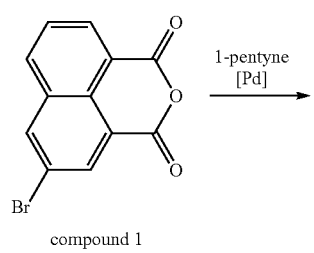

compound 1

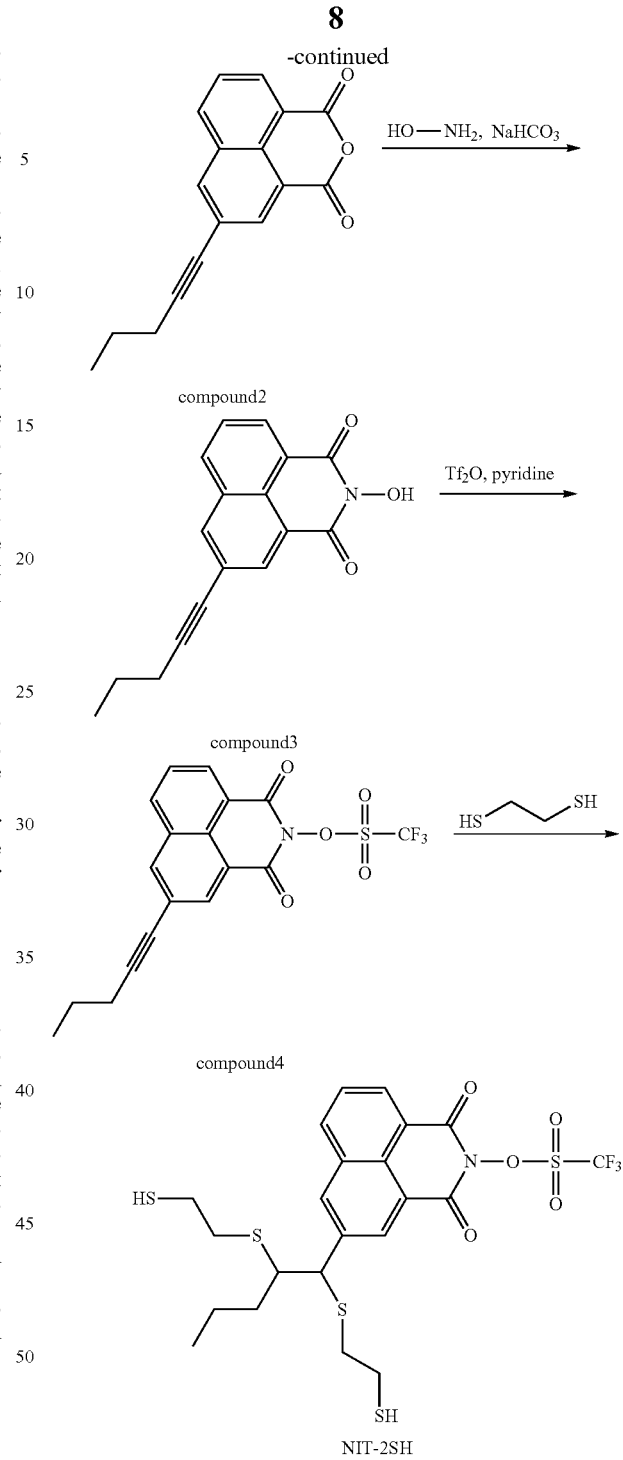

Through the above synthesis process, NIT-2SH was prepared. The specific synthesis process is as follows.

Synthesis of a Compound 2

Into a flask containing the compound 1 (1.0 equiv.), 1-pentyne (1.5 equiv.), palladium acetate (3 mol %), 1,3,5-triaza-7-phosphaadamantane (9 mol %), and cesium carbonate (1.5 equiv.) were added, and acetonitrile was introduced, and the solution was stirred at 80 □ for 24 hours. After the reaction was finished, water was added, and the solution was extracted three times with dichloromethane. An organic layer obtained after the extraction was dried with magnesium sulfate and filtered, and then the solvent was removed.

By purification by column chromatography, 23 g of the compound 2 was obtained with a yield of 85%.

Synthesis of a Compound 3 Into a flask containing the compound 2 (1.0 equiv.), HO—$NH_3Cl$ (hydroxylamine hydrochloride, 1.5 equiv.), and $NaHCO_3$ (1.5 equiv.) were added, and ethanol was introduced, and the solution was refluxed for 1 hour, and then the solvent was removed. Water and HCl (1N) were added, and the produced colorless solid was filtered, and then washed with diethylether to obtain 16 g of the compound 3 with a yield of 73%.

Synthesis of a Compound 4

The compound 3 (1.0 equiv.) was dissolved in chloroform, then pyridine (1.5 equiv.) was added, and the solution was cooled to 0° C. $Tf_2O$ (trifluoromethanesulfonic anhydride, 1.3 equiv.) was slowly added, and the mixture was stirred at room temperature for 3 hours. After the reaction was finished, water was added, the separated organic layer was washed with an aqueous solution of NaOH (0.2N), HCl (1N), and water, then dried with magnesium sulfate and filtered, and then the solvent was removed. By purification by column chromatography, 8.3 g of the compound 4 was obtained with a yield of 43%.

Synthesis of NIT-2SH

In a flask containing the compound 4 (1.0 equiv.), V-65 (1.2 equiv.) and 1,2-ethanedithiol (10 equiv.) were added, PGMEA was introduced, and a thiol-ene click reaction was progressed at 65° C. for 3 hours, thus preparing a compound of the structure of NIT-2SH. After the reaction was finished, water was added, the separated organic layer was washed with the water, dried with magnesium sulfate, and filtered, and then the solvent was removed. By purification by column chromatography, 3.1 g of NIT-2SH was obtained with a yield of 24%.

Comparative Preparation Example 1

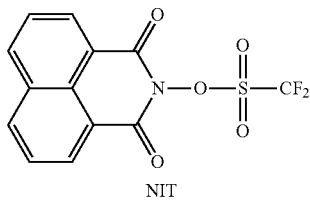

NIT

Commercially available.

EXAMPLES

Positive photoresist compositions of Examples 1 to 4 and Comparative Examples 1 to 5 were prepared with the components and contents described in the following Table 1. Here, the compounds represented by the following Chemical Formulas 9 and 10 are acrylic resins, the compound represented by the following Chemical Formula 11 is a PHS resin, NIT-2SH and NIT are photosensitive photoacid generator compounds (PAG), and Quencher is an acid diffusion inhibitor.

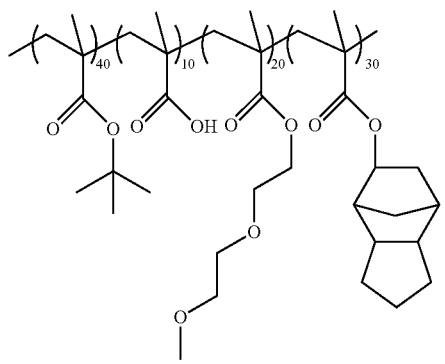

[acrylic resin 1, Chemical Formula 9]

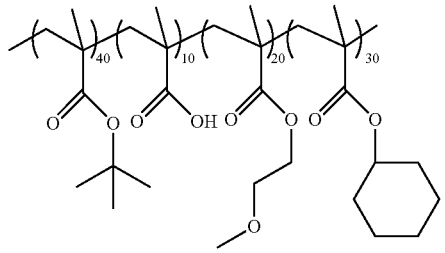

[acrylic resin 2, Chemical Formula 10]

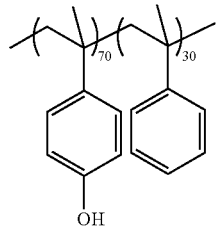

[Chemical Formula 11]

The components and contents of the photoresist compositions are shown in the following Table 1.

TABLE 1

|  | Example 1 | Example 2 | Example 3 | Example 4 | Comparative Example 1 | Comparative Example 2 | Comparative Example 3 | Comparative Example 4 |
|---|---|---|---|---|---|---|---|---|
| Acrylic resin 1 | 80 | 100 | 0 | 0 | 80 | 100 | 0 | 0 |
| Acrylic resin 2 | 0 | 0 | 80 | 100 | 0 | 0 | 80 | 100 |
| PHS resin | 20 | 0 | 20 | 0 | 20 | 0 | 20 | 0 |
| NIT-2SH | 3 | 3 | 3 | 3 | 0 | 0 | 0 | 0 |
| NIT | 0 | 0 | 0 | 0 | 3 | 3 | 3 | 3 |
| Quencher | 0.01 | 0.01 | 0.01 | 0.01 | 0.01 | 0.01 | 0.01 | 0.01 |

(unit: parts by weight)

Meanwhile, the contents described in Table 1 are based on solid content, the sum of the acrylic resin and PHS resin is 100 parts by weight, and NIT-2SH or NIT is respectively 3 parts by weight, and Quencher is 0.01 parts by weight, based on 100 parts by weight of the sum of the acrylic resin and PHS resin.

Performance Evaluation (1) Solubility

A time taken until the photoresist compositions prepared in Examples 1 to 4 and Comparative Examples 1 to 4 were completely dissolved after preparation, was evaluated according to the following standard. The results are shown in the following Table 2.

⊚: dissolved within 30 minutes after preparation
○: dissolved within 2 hours after preparation
Δ: dissolved within 8 hours after preparation
X: dissolved within 24 hours after preparation (2) Sensitivity On a Si substrate, the photoresist compositions prepared in Examples 1 to 4 and Comparative Examples 1 to 4 were spin coated and dried in a hot plate at 120 □ for 2 hours, and then exposed using a step mask, additionally dried in a hot plate at 100 □ for 2 minutes, and then developed in an aqueous solution of TMAH (tetramethylammonium hydroxide). The amount of exposure at which they were developed to the bottom without remaining scum was evaluated as sensitivity. The results are shown in Table 2.

(3) Anti-Corrosion Effect=Difference in the Footing of the Exposed Part after Development On a Si substrate, the photoresist compositions prepared in Examples 1 to 4 and Comparative Examples 1 to 4 were spin coated and dried on a hot plate at 120 □ for 2 hours, then exposed using a step mask, additionally dried in a hot plate at 100 □ for 2 minutes, and then developed in an aqueous solution of TMAH (tetramethylammonium hydroxide). A value reduced from the hole diameter of the top to the hole diameter of the bottom of the thick film resist pattern was measured as a footing length, which was an indicator of developability. The developability was measured according to the following standard, and the results are shown in Table 2.

⊚: footing length greater than 0 nm and less than 500 nm
○: footing length greater than 500 nm and less than 1 μm
Δ: footing length greater than 1 μm and less than 2 μm
□: footing length greater than 2 μm

TABLE 2

| | solubility | Sensitivity (exposure amount, mJ/cm$^2$) | Footing length |
|---|---|---|---|
| Example 1 | ⊚ | 340 | ⊚ |
| Example 2 | ⊚ | 510 | ○ |
| Example 3 | ⊚ | 380 | ⊚ |
| Example 4 | ⊚ | 550 | ○ |
| Comparative Example 1 | Δ | 740 | X |
| Comparative Example 2 | X | 990 | X |
| Comparative Example 3 | Δ | 800 | X |
| Comparative Example 4 | X | 990 | X |

From Table 2, it can be confirmed that the photoresist compositions according to Examples 1 to 4 of the present invention exhibit excellent effects in terms of solubility, sensitivity, and developability (anti-corrosion effect), compared to the photoresist compositions according to Comparative Examples 1 to 4.

The invention claimed is:

1. A photoacid generator represented by Chemical Formula 1:

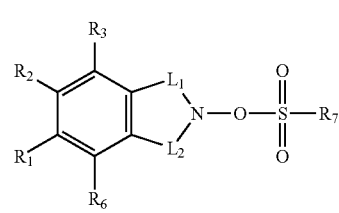

[Chemical Formula 1]

wherein, in the Chemical Formula 1, $R_1$, $R_2$, and $R_6$ are each independently hydrogen, or a $C_{1-10}$ alkyl group substituted with one or more $C_{1-20}$ alkylene dithiol groups, at least one of $R_1$, $R_2$, and $R_6$ is a $C_{1-10}$ alkyl group substituted with one or more $C_{1-20}$ alkylene dithiol groups, $L_1$ is a substituted or unsubstituted $C_{1-4}$ alkylene group that comprises a carbonyl connected to the nitrogen atom, or a carbonyl, $L_2$ is a carbonyl, $R_3$ is hydrogen, a $C_{1-20}$ aliphatic functional group, or forms a $C_{6-20}$ aromatic ring or a $C_{5-20}$ aliphatic ring together with $L_1$, and $R_7$ is a $C_{1-10}$ alkylfluoro group, a $C_{1-10}$ alkoxy group, or a $C_{1-10}$ alkylthio group.

2. The photoacid generator according to claim 1, wherein $R_3$ is a $C_{6-20}$ alkenylene group including at least one double bond and forms a C6-20 aromatic ring together with $L_1$.

3. The photoacid generator according to claim 1, wherein $R_3$ is a $C_{5-20}$ alkylene group and forms a C5-20 aliphatic ring together with $L_1$.

4. The photoacid generator according to claim 1, wherein $L_1$ is represented by Chemical Formula 2:

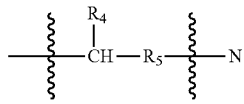

[Chemical Formula 2]

wherein, in the Chemical Formula 2, $R_5$ is a $C_{1-3}$ alkylene group that includes a carbonyl connected to the nitrogen atom, or a carbonyl, $R_4$ is hydrogen, a $C_{1-20}$ aliphatic functional group, or forms, together with $R_3$, one or more rings selected from the group consisting of benzene, naphthalene, and cyclohexane.

5. The photoacid generator according to claim 1, wherein the photoacid generator is one or more selected from the compounds represented by the following Chemical Formula 3 to Chemical Formula 5:

[Chemical Formula 3]

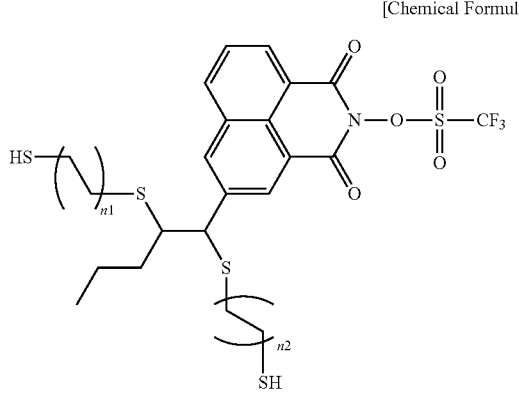

[Chemical Formula 4]

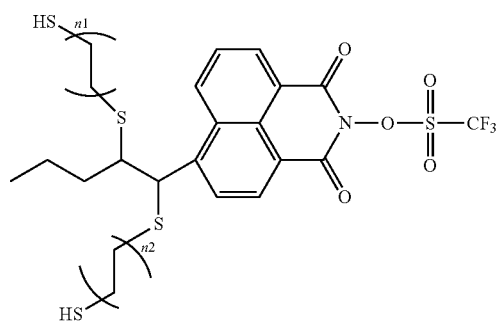

[Chemical Formula 5]

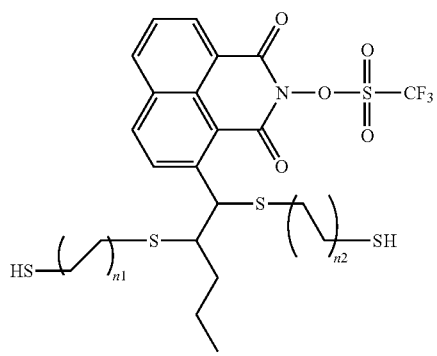

wherein, in the Chemical Formulae 3 to 5,
n1 and n2 are each independently an integer, and $1 \leq n1 \leq 20$ and $1 \leq n2 \leq 20$.

6. A chemically amplified photoresist composition for a thick film, comprising the photoacid generator of claim 1.

7. A chemically amplified photoresist composition for a thick film, comprising the photoacid generator of claim 2.

8. A chemically amplified photoresist composition for a thick film, comprising the photoacid generator of claim 3.

9. A chemically amplified photoresist composition for a thick film, comprising the photoacid generator of claim 4.

10. A chemically amplified photoresist composition for a thick film, comprising the photoacid generator of claim 5.

* * * * *